United States Patent

Rising et al.

[11] Patent Number: 5,221,311
[45] Date of Patent: Jun. 22, 1993

[54] EVACUATED SAMPLING VIAL

[76] Inventors: Peter E. Rising, 132 Wilbur Pl., Bohemia, N.Y. 11716; Peter G. Chaconas, 11607 Hitching Post La., Rockville, Md. 20852

[21] Appl. No.: 818,895

[22] Filed: Jan. 10, 1992

[51] Int. Cl.⁵ .................................. C03B 23/57
[52] U.S. Cl. .................................... 65/102; 65/54; 65/110; 65/282; 422/61; 422/99; 422/100; 422/102; 215/32
[58] Field of Search ............... 422/102, 99, 100, 58, 422/61; 73/864.52, 864.02, 864.82; 215/32; 206/0.7; 53/405, 403, 408, 478; 65/54, 102, 109, 110, 282

[56] References Cited

U.S. PATENT DOCUMENTS

| | | | |
|---|---|---|---|
| 1,594,370 | 8/1926 | Kubota | 422/100 |
| 1,956,568 | 5/1934 | Fjord | 215/32 |
| 1,967,603 | 7/1934 | Zimber | 65/109 |
| 3,078,694 | 2/1963 | Schoenmakers | 65/109 |
| 3,272,366 | 9/1966 | Ikeda | 215/32 |
| 3,523,017 | 8/1970 | Tatibana | 65/109 |
| 3,688,812 | 9/1972 | Fredericks | 215/32 |
| 3,719,463 | 3/1973 | Lewis | 215/32 |
| 3,915,014 | 10/1975 | Judge et al. | 73/864.52 |
| 3,951,855 | 4/1976 | Principe et al. | 73/864.52 |
| 4,445,390 | 5/1984 | Atwell | 73/864.52 |
| 4,537,747 | 8/1985 | Castaneda | 73/864.52 |

*Primary Examiner*—Robert J. Warden
*Assistant Examiner*—Hien Tran
*Attorney, Agent, or Firm*—Leonard Belkin

[57] ABSTRACT

An evacuated vial for collecting a fluid sample and a method for manufacturing the vial comprising a cylindrical glass tube, one end of the tube formed into a frangible tip, a glass bottom closing off the other end of the tube, and a depression formed in the bottom forming an internal breaking tip extending into said tube. The bottom of the tube is sealed in a manner permitting convenient puncture thereof to break the tip when a sample is to be delivered.

11 Claims, 3 Drawing Sheets

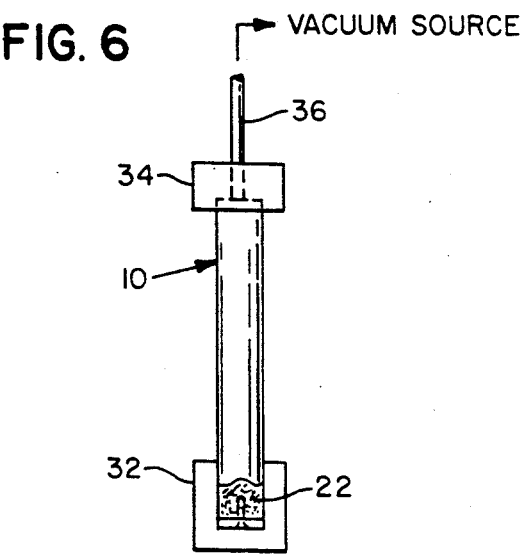
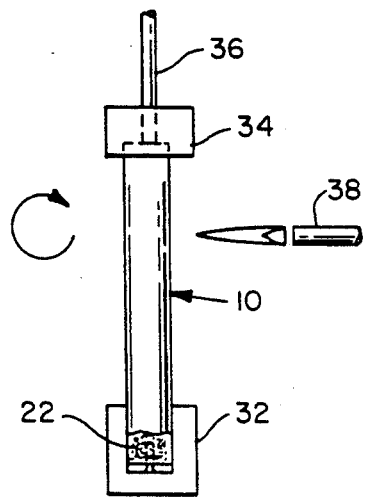
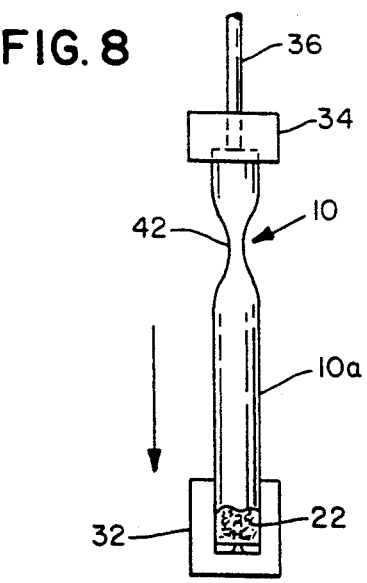
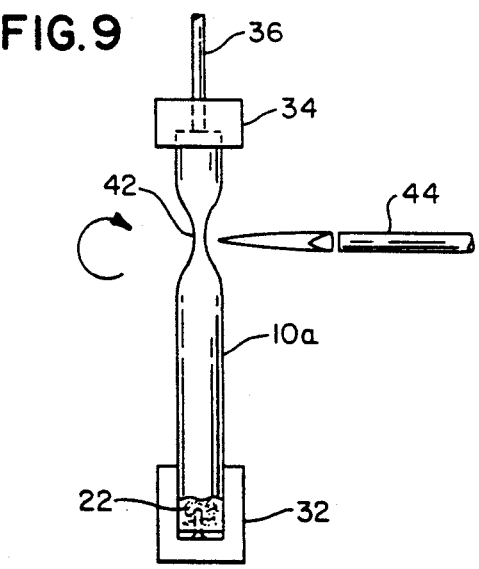
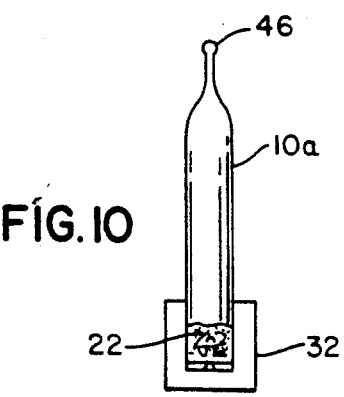

EVACUATED SAMPLING VIAL

BACKGROUND OF THE INVENTION

The present invention relates to a vacuum sampling vial and more particularly to a vacuum sampling vial capable of safe sample extraction in only a single step.

With the advance of quantitative laboratory measuring techniques to easily and accurately measure certain ionic species such as heavy metals (i.e., Pb, Fe, Cu) in ultra low ranges (0-25 ppb) the need to obtain water samples which are truly untainted has increased many fold.

To date, water sampling technologies for trace level water samples require a skilled operator to extract a sample because of the handling of hazardous materials used to stabilize water samples and the need to prevent exposure to contaminants introduced from unclean vessels or implements. The risk of sample contamination is so great for extreme low level measurements that sterilized sampling containers once opened to permit the sample to be placed in it can be contaminated by exposure to surrounding environmental conditions. Additionally, once the sample has been extracted and inoculated with a stabilizer such as concentrated nitric acid for copper samples, a product results which has personal and transportation hazards.

For example, to test for the presence of the element copper in water via the use of an ICP (Inductively Coupled Plasma) analyzer, the currently available sampling systems provide for a multi step extraction procedure before the ICP can perform its analysis. Steps involved are the filling of a copper free bottle with water, sample inoculation with copper free nitric acid, extraction of the sample from the sample container via copper free apparatus such as a pipetter and resealing of the sample container without contamination and for eventual environmentally safe disposal of the excess acidified sample. The entire procedure can take hours.

In our patent application Ser. No. 07/781,875 entitled "Vial With Powdered Reagent" filed on Oct. 24, 1991, we describe a method of manufacturing an evacuated vial containing a powdered reagent under conditions in which contamination is avoided so that the vial can be stored for an indefinite period of time. Once the frangible tip is broken and the vial is filled with a sample and taken to a laboratory for analysis. If it were desired to remove the sample, the sample will not leave the vial merely by unsealing the neck due to the narrow diameter of the opening so that destruction of the vial itself is required with the attendant risks of contamination. Hence, so that the use of such an evacuated vial either requires a more expensive procedure to avoid the contamination or the use of such a vial is limited to circumstances where contamination is not considered to be a problem.

In other words, evacuated sampling vials are not useful where high levels of purity and accuracy are required due to the inability to transfer the sample from the vial to the testing apparatus without risk of contamination.

A number of United States Patents teach sampling methods and apparatus for testing purposes.

U.S. Pat. No. 3,332,288 discloses a device for sampling molten metal using an elongated tube which is evacuated and has a weakened portion which breaks when thrust into the metal. The tube is made by glass blowing.

U.S. Pat. No. 3,626,762 shows a method and apparatus for filling a capillary tube with liquid in which a wedge device is employed to break the frangible tip of the tube.

U.S. Pat. No. 4,445,390 discloses a sampling tube and apparatus for use in detecting the presence of hydrogen in a molten specimen. A porous plug is employed within the tube through which the hydrogen passes.

U.S. Pat. No. 4,537,747 teaches a disposable sampling device in which an evacuated vial with a frangible tip is employed. The sample is then shaken out of the vial for testing.

None of the preceding patents teaches the present invention.

SUMMARY OF THE INVENTION

In this invention there is provided a sampling vial particularly useful where the need to avoid contamination is great and a method of manufacturing such a vial.

In a preferred embodiment of this invention the sampling vial is evacuated with a frangible tip at one end for receiving the sample. The other end of the vial is provided with an internal breaking tip which is readily punctured to permit the sample to be removed through the tip.

The method of manufacturing the vial according to a preferred embodiment involves cutting a preformed glass tube to a fixed length, forming a flat glass bottom at one end, heating a small circle in the glass bottom, pressing a tungsten plunger into the heated circle creating an internal breaking tip, and dipping the glass bottom with the internal breaking tip in a plasticized bath to form a seal. In an alternative embodiment, an ultra thin glass bottom is mounted on and sealed over the internal breaking tip. The other end of the vial is then formed into an external tapered tip in accordance with the method described in our patent application identified above.

It is thus a principal object of this invention to provide a sampling vial of unique design and manufacture for use in sampling liquids with minimum risk of contamination.

Other objects and advantages of this invention will hereinafter become obvious from the following description of preferred embodiments of this invention.

BRIEF DESCRIPTION OF THE DRAWINGS

FIGS. 6-10 are diagrammatic views of the steps involved in sealing the load filled vial under vacuum.

DESCRIPTION OF THE PREFERRED EMBODIMENTS

Figure 1:
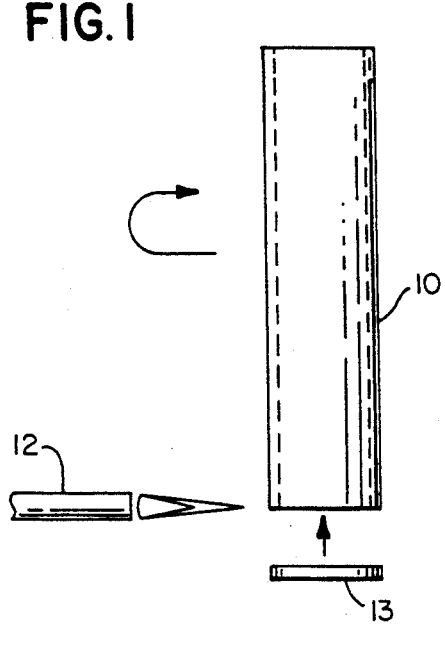
FIGS. 1 to 4 are diagrammatic views of the steps involved in adding a bottom to a tube to form a vial incorporating the principles of this invention.

Referring to FIG. 1, a hollow, preformed glass tube 10 cut to a fixed length is provided with a glass bottom by heating one end of tube 10 using a burner 12 and welding a glass blank 13 to the bottom of tube 10 as shown in FIG. 1.

Figure 2:
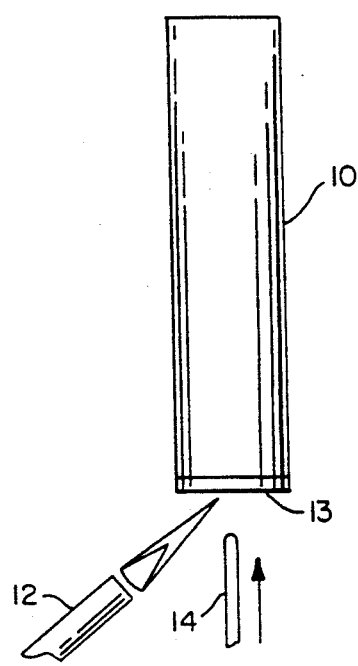
Figure 3:
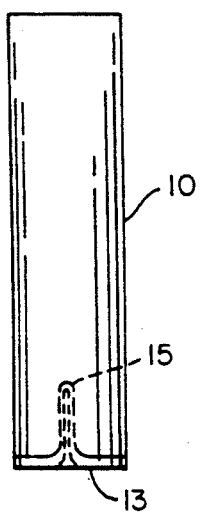

As seen in FIG. 2, bottom 13 is heated in the center, typically, a 5 mm circle, to about 750 degrees F. A tungsten plunger 14 is pressed in and through glass bottom 13 to a prescribed depth (dependent on the width and vacuum pressure) creating an internal breaking tip 15 in the bottom of tube 10 as seen in FIG. 3. This operation must take no more than 0.5 seconds. Properly done, as will be seen later, a sample release mechanism has been created which is both sturdy enough to withstand the application of a vacuum and transportation of a filled vial yet frangible enough to be broken by a lab technician in a controlled manner.

Having now created an open ended tube 10 with internal release point 15, open ended tube 10 is heated to 800-1000 degrees F. for a period of 6 hours to clean it of potential contaminants.

Figure 4:
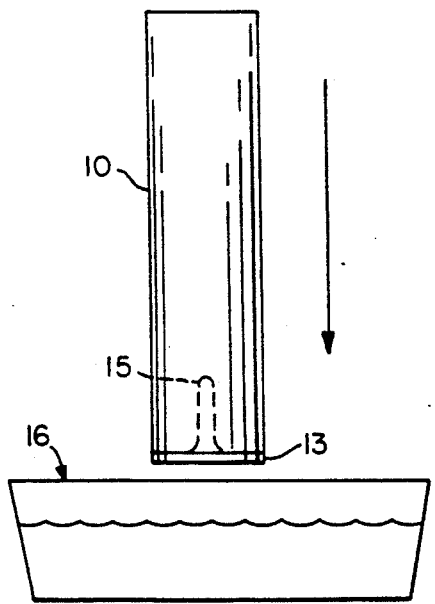
Figure 4A:
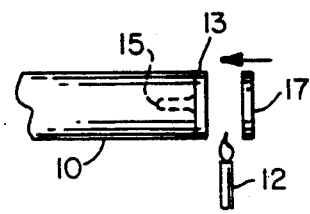
FIG. 4a is a diagrammatic view of an alternative embodiment.

Next the closed end with the internal break point 15 is dipped in a plasticized sealant bath 16 as seen in FIG. 4 forming a membrane over the closed bottom of tube 10. If desired, as an alternative, an ultra thin glass bottom 17 is attached as seen in FIG. 4a. This step is necessary to assure no contamination enters the sample during sample release. The choice of end seal will be dependent on sampling application.

Figure 5:
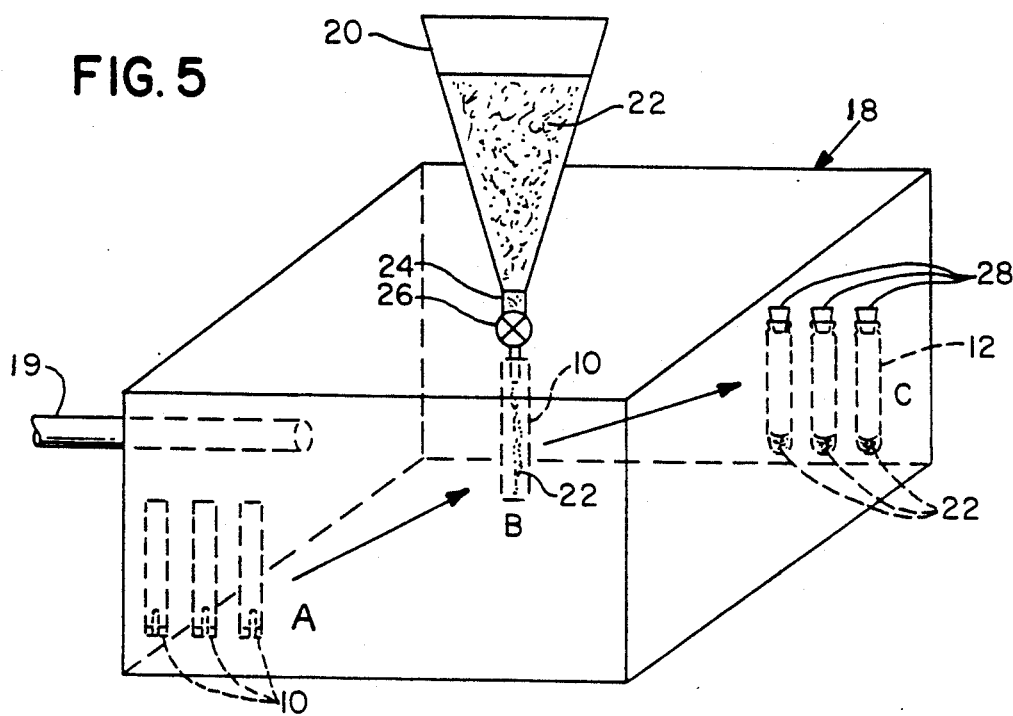
FIG. 5 is a diagrammatic, schematized view of a glove box in which the close bottomed tubes are supplied with mixture, and sealed

Referring to FIG. 5, clean open at the top tubes 10 are then placed inside of a glove box 18 containing an inert gaseous medium such as nitrogen gas supplied by and maintained at an overpressure through a hose 19.

Mounted on glove box 18 is a sealed funnel herein referred to as retention vessel 20 containing a previously prepared highly purified mixture 22 of a stabilizing agent or reagent having an outlet tube 24 extending into glove box 18. Within glove box 18, tube 24 is provided with a stopcock 26, which, as is understood in the art, each rotation thereof would release a predetermined measured amount of mixture 22 into the open mouth of tube 10 directly underneath, the details of which are described in our earlier application identified above.

As is understood in the art, the worker would reach into glove box 18 using gloves (not shown) to fill a number of tubes, or as now hereinafter referred to as vials 10 with the measured amount of mixture 22 of the reagents, followed by closing off each vial 10 with a stopper 28. A vial 10 in position A would be moved to position B directly underneath tube 24, filled with mixture 22, then stoppered and moved to position C.

A number of vials 10 closed off with mixture 22 contained therein are removed from glove box 18 and handled in a manner to be described.

Referring to FIGS. 6-10, each vial 10 containing mixture 22 is placed upright with its bottom inserted for support in a hollow closely fitted base 32. Stopper 28 is removed and immediately replaced by a cap 34 which seals and grasps the top, and is attached to a vacuum hose 36 connected to a suction pump (not shown) or other source of vacuum to evacuate the interior of vial 10 leaving only nitrogen under less than atmospheric pressure.

As seen in FIG. 7, a flame nozzle 38 jets a flame to make contact with an intermediate portion of vial 10 while base 32 is rotated to cause vial 10 to spin so that it is heated uniformly around the circumference. After the glass is softened in the region heated, as seen in FIG. 8, cap 34 is pulled upwardly to stretch vial 10. Heat is controlled carefully to insure that the glass is softened only enough to permit the elongation. The softened portion under the influence of the vacuum is drawn inwardly to form a narrow waist 42.

In the next step, seen in FIG. 9, a flame nozzle 44 is employed to heat a very narrow portion of waist 42 until total collapse takes place sealing off the bottom portion 10a of vial terminating in a sealed tip 46. Cap 34 with the top portion of vial 10 is removed. The bottom portion, now referred to as vial 10a, containing the stabilizing agent 22 under vacuum is then removed from base 32 and may be otherwise prepared for use, i.e., labelling, scoring of the tip, etc.

The result of the preceding steps is a sealed vial or ampule 10a containing an inert gaseous medium such as nitrogen under a subatmospheric pressure and a stabilizing agent or reagent where required.

Figure 11:
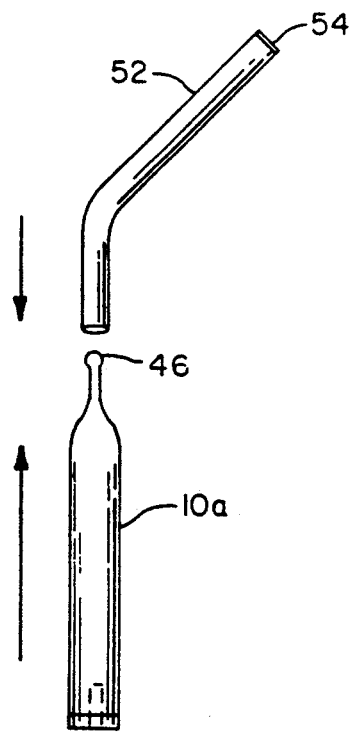
FIGS. 11 and 12 are diagrammatic views of the steps involved in preparing the frangible tip of the vial for use.
Figure 12:
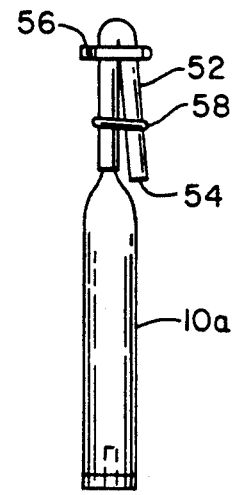

Referring to FIGS. 11 and 12, a plastic sampling hose 52, previously chemically rinsed to remove any contaminants, is applied over the external tip 46. The open end 54 of hose 52 is hermetically heat sealed closed, and is folded in half. If desired, a hose clamp 56 may be applied at the fold point and a ring 58 slipped over the folded hose.

Sealed vial 10a with the plastic sampling hose 52 attached is then placed under a rotating UV light source as is understood in the art to kill any bacterial contaminants and then packaged for shipment.

To use vial 10a to obtain a sample, vial hose 52 is straightened by removing clamp 56 and ring 58, the sealed tip 54 is snipped off, and the straight hose is inserted into the water to be sampled. Vial tip 46 is snapped by the operator using his fingers to squeeze hose 52. The vacuum applied during manufacture causes a sample to be drawn into vial 10a. The operator then folds vial hose 52 and reapplies the hose clamp and ring 58 for transportation back to the lab facility. The hose will act as a pressure compensator arising from temperature changes during transportation and storage.

It is seen that the extraction of the sample occurs without the exposure to contaminants or personal hazard to the operator. Additionally, the operator need not be of special skill or education.

Once at the laboratory, the lab technician removes the hose clamp 56 and cuts the plastic hose 52 off to open it up. Holding vial 10a in the inverted position and directly over the ICP sample chamber or other testing device, the technician depresses the center of the membrane or penetrates the thin glass bottom 17 covering the flat bottom of the vial with a plastic rod. This causes the very unique internal release point 15 to break and permits the sample to flow freely into the ICP sample chamber.

The entire procedure of sample extraction and sample loading takes a minute without permitting contact to outside contaminates where current technologies can take hours of a skilled technician's time.

This unique sampling arrangement is applicable to a multitude of different elemental tests in water and may have application in the future for gaseous elements as well. It is understood that the vial can be used for extracting liquid samples only and not containing any stabilizing agent or reagent. This would be accomplished by using glove box 18 in FIG. 5 only to provide the inert atmosphere and not to insert the mixture.

It will be seen that the novel sampling vial and the attendant methods of manufacture and use afford many advantages over previous vial designs. It provides a sterilized container with indefinite shelf life and a one step procedure for sample extraction in which there is an easy and non contaminating method of removing the sample from the sampler into the laboratory analytical vessel thus eliminating any operator introduced contamination. Also, the use of this vial eliminates hazardous material classifications for both operator and transportation.

While only certain preferred embodiments of this invention have been described it is understood that many variations of this invention are possible without departing from the principles of this invention as defined in the claims which follow.

What is claimed is:

1. A vial for collecting a fluid sample comprising tube means containing a gas medium under less than atmospheric pressure having first and second ends, the first end of said tube means formed into a closed frangible tip outside of said tube means constructed and arranged to be broken when a sample is to be collected, bottom means closing off the second end of said tube means, a closed internal breaking tip formed in said bottom means extending into said tube means and being breakable at the internal breaking tip within said vial, and means sealing the bottom means of said tube means constructed and arranged for permitting convenient access to and puncture thereof to afford access to break said internal breaking tip when a sample is to be dispensed.

2. The evacuated vial of claim 1 wherein said sealing means is a thermoplastic sealant.

3. The evacuated vial of claim 1 wherein said sealing means is a sheet of frangible material mounted on said bottom means to enclose said internal breaking tip.

4. The evacuated vial of claim 1 wherein said vial contains a powdered reagent or stabilizing agent for mixing with said fluid sample.

5. The vial of claim 1 in which said tube and bottom means are glass.

6. The vial of claim 1 containing a reagent to react with said fluid sample and said gas medium comprises an inert gas.

7. A method of making an evacuated vial from a tube means having first and second ends for collecting a fluid sample comprising the steps of sealing the first end of said tube means with a glass bottom means, placing an inert gas into said tube means, sealing the second end of said tube means with a closed frangible tip for collecting said fluid sample while maintaining within said tube means said inert gas and reducing a pressure there to less than atmospheric and evacuating said tube means, forming in said glass bottom means a closed internal breaking tip located entirely within said tube means, said internal breaking tip being breakable within said vial, and sealing said internal breaking tip in a manner which permits penetration for the convenient breaking of said internal breaking tip for dispensing the collected fluid sample.

8. The method of claim 7 wherein said internal breaking tip is sealed by dipping said bottom means in molten thermoplastic material.

9. The method of claim 7 wherein said internal breaking tip is sealed by enclosing said internal breaking tip with a thin sheet of glass welded to said bottom means.

10. The method of claim 7 wherein an ultra pure reagent or a stabilizing agent is sealed within said vial when said inert gas is placed within said vial.

11. The method of claim 7 wherein said tube and bottom means are glass, forming said internal breaking tip in said bottom means by heating a portion of said bottom means until soft and applying a rod to the soft portion of said bottom means to form an indent in said bottom means, the wall of indent being thin enough to permit breaking by imposing the end of a rod yet thick enough to endure the vacuum within said vial.

* * * * *